United States Patent [19]

Weinrib

[11] Patent Number: 4,706,671
[45] Date of Patent: Nov. 17, 1987

[54] CATHETER WITH COILED TIP

[76] Inventor: Harry P. Weinrib, 2644 W. Estes Ave., Chicago, Ill. 60645

[21] Appl. No.: 730,322

[22] Filed: May 2, 1985

[51] Int. Cl.⁴ .............................................. A61M 25/00
[52] U.S. Cl. ................................. 128/348.1; 128/341; 604/104
[58] Field of Search ..................... 128/341, 343, 348.1, 128/345; 604/104, 264, 272, 8, 281

[56] References Cited

U.S. PATENT DOCUMENTS

| | | | |
|---|---|---|---|
| 207,932 | 9/1878 | Alvord | 128/341 |
| 216,396 | 6/1879 | Guest | 604/104 |
| 4,471,778 | 9/1984 | Joye | 128/341 |
| 4,503,569 | 3/1985 | Dotter | 128/334 R |
| 4,531,933 | 7/1985 | Norton et al. | 604/8 |
| 4,553,545 | 11/1985 | Maass et al. | 128/341 |

FOREIGN PATENT DOCUMENTS

| | | | |
|---|---|---|---|
| 129634 | 1/1985 | European Pat. Off. | 128/348.1 |
| 584856 | 12/1977 | U.S.S.R. | 128/348.1 |
| 1115757 | 9/1984 | U.S.S.R. | 128/341 |

Primary Examiner—Gene Mancene
Assistant Examiner—Cary E. Stone
Attorney, Agent, or Firm—Fitch, Even, Tabin & Flannery

[57] ABSTRACT

A catheter is provided with a coil section at the distal end which is stretched initially into a generally linear insertion position for moving inwardly a vessel, such as a blood vessel, to an operative location at which the coil section is re-formed with a larger diameter, preferably in the form of a hollow conical scoop to scoop clot material from the blood vessel. The coil section is stretched into the general linear insertion configuration by an internal wire which may be removed leaving a hollow passageway in the tube which can be stiffened by the application of fluid pressure such as a liquid to stiffen the coils. This assists in pulling the clot material from the vessel as the elastomeric material of the coils slides across the blood vessel walls without damaging the same. The preferred embodiment has two separate wire members associated with the flexible elastomeric tube of the catheter.

16 Claims, 4 Drawing Figures

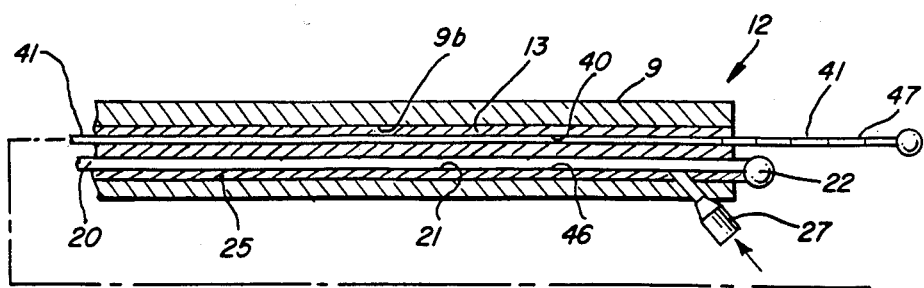
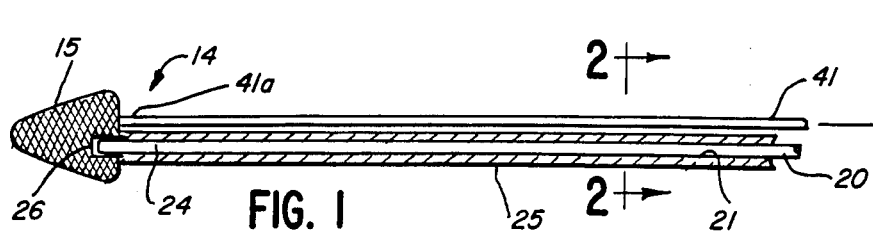
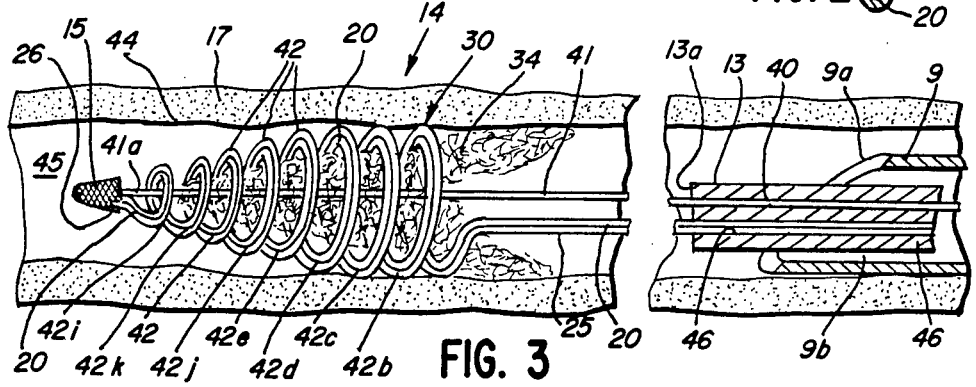
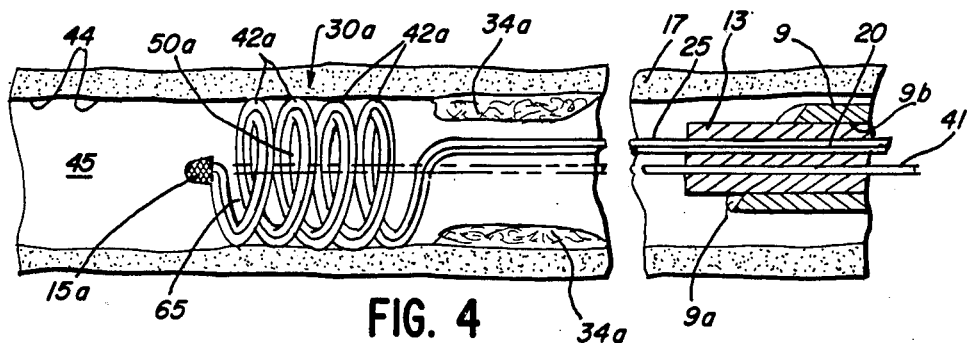

4,706,671

CATHETER WITH COILED TIP

This invention relates to a catheter and more particularly to a catheter for positioning within the living vessels of human beings.

In modern medical practice, there is extensive use of balloon catheters many of which are used for dilatation of arteriosclerotic plaque or atheroma. In such balloon catheters, there is an elongated body having a balloon at the distal end with a wire like member inserted through the catheter to aid the surgeon in guiding the balloon to the location at which the dilatation is to occur. The catheter also has a conduit or passageway therein which is connected at one end to the balloon for expansion thereof and which at the opposite end is connected to a syringe or other device for applying an incompressible fluid under pressure to the balloon to expand the same. The pushing of the plaque material into the side walls of the vessel is not as desirable as removing it, but it is used to open the vessel where there is substantial closing thereof by the plaque material.

In other instances, the balloon catheter is used to try to remove embolisms or blood clot material which is usually in the form of a relatively thick jelly like substance. After the balloon is projected through the clot material, the balloon is expanded and then the catheter is pulled while trying to pull the embolism material in front of the catheter to pull the clot from the vessel. Manifestly, some of the embolism material may be pushed into the side walls or into branches of the vessel as it is being pulled from a location in the body to an incision into the vessel. Thus, there is a need for a new and improved catheter which can remove clot material or be used for dilatation or for other purposes.

Accordingly, an object of the present invention is to provide a new and improved catheter of the foregoing kind. Another object of the invention is to provide a catheter which will collect and trap an embolism and allow it to be pulled from the living vessel in an improved manner.

These and other objects and advantages of the invention will become apparent from the following detailed description taken in connection with the accompanying drawings:

FIG. 1 is a cross-sectional view taken through a catheter constructed in accordance with the preferred embodiment of the invention;

FIG. 2 is a cross-sectional view taken substantially along the line 2—2 of FIG. 1;

FIG. 3 is an enlarged fragmentary view showing a spiral coil portion of the catheter in its expanded operative position;

FIG. 4 illustrates another embodiment of the invention having a coil of substantially constant diameter in its expanded operative position;

As shown in the drawings for purposes of illustration, the present invention is embodied in a catheter 10 which includes a needle 9 having a pointed, sharp end 9a (FIG. 3) for making an incision into a living vessel. Inside of the needle 9 is a tubular catheter body 13 formed of a molded elastomeric material having internal passageways to be described hereinafter. The diameter of catheters is related to the size of the living vessel into which it is to be inserted. The present invention is directed to catheters of various sizes but is particularly directed to catheters of very small size which may be smaller than the diameter of the femoral artery which allows insertion of catheters into the aorta. Smaller size catheters also may be used for insertion through the carotid artery into the brain in which are blood vessels of a small size. The present invention is adapted for use with vessels which may be as small as 0.3 mm. The catheter extends from a proximal end 12 to a distal end 14 to which is fixed a solid tip 15 which may be a bullet or conical shaped end for smoother guiding of the distal end 14 of the catheter into and through a living vessel 17, as best seen in FIGS. 3 and 4. The thin and small diameter catheter is usually not sufficiently rigid to be inserted and guided through relatively long distances without the inclusion of a stiffening or support member usually in the form of a wire member or wire 20 which in this instance is inserted through an elongated hollow passage 21 formed in the body between the proximal end 12 and the distal end 14. More specifically, it is preferred to have the elongated wire 20 extend from a free end 22 extending outward of the body 11 to a distal end 24 to which the wire is releasably connected at a socket 26 in the tip 15. During insertion of the catheter, the wire member 20 is pushed and guided to slide the catheter through the vessel often while the surgeon is viewing it under a fluoroscope or like device. Upon reaching the desirable location the wire member 20 is pulled outwardly from the catheter with the distal end 24 of the wire being pulled from the socket 26 in the tip 15. The entire wire 20 is pulled from the catheter leaving the passageway 21 hollow for insertion of a liquid, as will be explained hereinafter.

In addition to the above, balloon catheters often have a syringe receptor socket 27 which communicates with a fluid passageway such as a passageway 21 to allow a syringe or other device containing an incompressible fluid or liquid to be inserted through the passageway to pressurize the balloon at the distal end of the catheter. The balloons suffer from a number of problems and shortcomings one of which may be that the balloon is eccentrically formed with the result that one side of the balloon is expanded to a greater diameter than the other side so there is not an equal expansion about the axis of the catheter. Such an unequal expansion in diameter may exert sufficient localized pressure to burst the vessel wall and cause damage. Additionally, the balloons are usually formed of a different material and more flexible elastic material than the catheter body such that the balloon is formed as a separate piece which is adhered by adhesives to the catheter body. The use of adhesives and the separately formed balloon and the fabrication step of adhering the balloon to the catheter body adds substantially to the cost of the balloon catheter and also represents a potential source of failure if the adhesion process is faulty.

As above described, these conventional balloon catheters are generally satisfactory, but often their use forces the arteriosclerotic plaque into the walls rather than scrapping or removing the same from the area. Further, the balloon when it is used to remove an embolism or clot pushes the clot material before it has a tendency to force the clot material into and against the side walls of the vessel and into branches intersecting the vessel. The balloon does not form a good collector for the jelly like clot material.

In accordance with the present invention, there is provided a new and improved catheter which has a unique coil section 30 at the distal end 14 of the catheter with the coil section being uncoiled and stretched into a general linear insertion position for providing a smaller diameter during insertion into and through a blood vessel, such as is shown in FIG. 1, and which can be shifted into its operative position at which the coil section is formed with a large diameter, as shown in FIGS. 3 and 4. More specifically in accordance with the present invention, the wire member 20 is forced forwardly into the catheter and extends the tip 15 to pull the coils forwardly and to uncoil individual coils 42 of the coil section leaving a straight substantially linear shape for the coil section. In this straight small diameter insertion position, it is preferred that no coils 42 are present or visible as the coil section 30 is being guided through the living vessel to the location at which may be a clot or embolism material 34 or 34a as shown in FIGS. 3 and 4. Upon penetrating through the clot material the wire member 20 is released and pulled rearwardly towards the proximal end catheter end allowing the memory of the coils 42 to cause each of them to return to its natural coiled condition. In the preferred embodiment of the invention as shown in FIG. 3, the coiled section 30 is conical or helical which shape can serve as a scoop collector or trap to gather the embolism material 34 for pulling through the living vessel 17 for its removal. Since the embolism material is a relatively thick jelly like material, it will stay within the coil collector section 30. In the second illustrated embodiment of the invention, shown in FIG. 4, the coil section 30a is formed with substantially identical shaped coils 42a each of a constant diameter. The coils 42 or 42a because they are separated from one another and are spaced from each other may flex or bend to more readily accommodate irregularities or non-constant diameter portions 44 in the vessel wall 45.

The diameter of the coil section can be varied by the operator pushing or pulling on a wire member 41 which is permanently fixed at its distal end 41a to the tip 15 and which extends through or along side of the coil section 30 or 30a to the catheter body 13 and through the latter to be gripped at its outer proximal end 47, as best seen in FIG. 1. As can be appreciated pushing of the wire member 41 to displace the tip forwardly, i.e. to the left as viewed in FIG. 3, reduces the diameter of the coils 42 and of the conical coil section 30. Conversely, pulling of the wire member 41 moves the tip 15 toward the needle 9 and causes the coils to enlarge their diameter. This pushing and pulling movement also functions to change the pitch distance or spacing between adjacent coils.

In accordance with the preferred embodiment invention the coil section 30 may be stiffened or hardened under the control of an operator by means forcing an incompressible liquid into the hollow passageway formerly occupied by the wire 20 and exertion of hydraulic pressure from a liquid receptor 27. That is, the liquid is forced by a syringe through the passageway to exert a hydraulic force within the coils of the coil section to stiffen the same.

Referring now in greater detail to the illustrated embodiment of the invention, the catheter 10 has a hollow tubular needle 9 at the location of the incision and the usual catheter body 13 lies within the needle bore 9b. The catheter body 13 is tubular and is molded of a plastic or rubber-like material with two bores or passageways 40 and 46 therein. The silastic tubular member 25 is preferably pulled through the bore 46 in the catheter body 13 and is connected to the syringe with the wire member 20 therein extending through the body member and needle. The second integrally formed bore 40 in the catheter body 13 receives therein in sliding relationship the wire member 41 which extends to the tip 15. The pushing and pulling of the wire member slides it within the bore and changes the diameter of the coils 42 in the coil section. The catheter body 13 may be substantially longer than illustrated herein at which the body terminates at an end 13a (FIG. 3) closely adjacent the needle tip 9a. On the other hand, the tubular member 25 may extend several feet beyond the body end 13a. The catheter body is preferably of a different material than the tubular body which is preferably formed of silastic.

The preferred silastic material used for the tubular member 25 is usually extruded in a very long continuous tube and the passageway 21 is defined by an integral wall or hollow bore formed during the extrusion process. The bore or passageway 21 extends longitudinally from the proximal end 12 into and through the coil section 30 so as to form a passageway interior within individual the coils 42 into which an incompressible fluid may be admitted as through the syringe receptor 27 to stiffen the coil 30 to the desired stiffness. If it is thought that the coils 42 are too hard, then the amount of pressure may be reduced. The silastic material is very soft and the coils should not damage the vessel side walls 46 when encountering bumps 44, plaque or other conditions in the side walls 45 in the vessel, as best seen in FIG. 3. Likewise, the individual coils 42 or 42a because of their spiral nature and because of their large central openings 50 within the coil may be compressed individually toward the center of the vessel and the coils are allowed to expand and contract with fluctuations with size in the vessel lumen. In the preferred embodiment illustrated in FIG. 3, the larger coils 42b, 42c of the coil section are spaced remotely from the tip 15 while the smaller diameter coils 42i and 42h are disposed closest to the tip 15. In this manner, the clot material or whatever is being removed will have a tendency to be scooped and collected and gathered and to be stopped from flowing through the coil by the smallest diameter coils and tip 15. At the other end of the coil section 30, the large circular opening 50 encircled by the first coil 42b provides a large opening or scoop for collecting the material which could be a plaque material or embolism material. The particular use of the catheter may be varied considerably from that described herein and still fall with the purvue of the present invention as defined by the appended claims. The number of coils and the pitch of the helix may be changed substantially from that illustrated herein. By way of example, the longitudinal length of the coil section 30 may be about one-quarter inch to one inch with the maximum diameter of the coils being 1.4 mm when the catheter has a 0.5 mm tubular body.

The illustrated tubular member 25 is a very long one piece tube formed of silastic by an extrusion process which leaves a hollow interior passageway 21 into which will be inserted the wire member 20. The wire member may be quite small, e.g. a 0.2 mm diameter wire within a tubular member having an outer diameter of 0.3 mm. Typically, the catheter for use in blood vessels may be provided in a range of sizes. The very small 0.3 mm tubular body may be used in vessels from about 1.0 mm to 5.0 mm in diameter. The coil section 30 may have its diameter extended to 5 mm by pulling on the wire member 41 to enlarge the diameter of the coils 42. Likewise, a tubular body 25 of about 5 mm can be used for a range of blood vessels of 5 to 12 plus millimeters in diameter. Thus, it is possible to reduce the inventory of catheters to be stocked and inventoried because of the ability to change coil diameter with the present invention. Because the tubular body 25 can be molded in one piece with only one coaxial bore therein, it can be manufactured very inexpensively. Rather than pulling the tubular body 25 through the bore 46 in the catheter body 13, connector flanges may be provided on the tubular body's end for connection to a connector flange on the catheter body end 13a. The distal end of the tubular body may be adhered or otherwise fastened to the tip 15.

The preferred method of forming the coil 30 section is to form coil section during the extrusion process so that as the coil section is cooled it will retain a memory that is, the elastomeric material will have been molded with tension and compression forces therein which will want to retain the elastomeric material in the shape of coils. Thus, when tension forces exerted by the wire member 21 are removed therefrom, and when the coil section is at generally ambient conditions or the temperature of the human body in which it is located, the coil section will return to the shape and size at which it was formed. Another alternative method of forming the coil section 30 is to take a small portion of the tubular body and to wrap the coil around a heated mandrel to heat the coiled section 30 on the mandrel up to and adjacent the extrusion temperature and to leave the coil section on the mandrel for a length of time. Thereafter, while leaving the coil section on the mandrel, the elastomeric material may be cooled so that after the elastomeric material is cooled it will take the coiled condition desired.

In the embodiment illustrated in FIG. 4 the coils are formed of a substantially constant diameter which each of the coils 42a being of the same pitch and of the same diameter with a hollow opening 50a within the coils. The constant diameter coil may be used for dilatation where there is plaque material 34a closing the lumen. The spacing of the coils allows the same to be expanded and turned and to be removed with less damage to the vessel wall 45 than with a typical balloon which lacks any accommodations for variations in diameter.

The coil section 30a of the constant diameter shown in FIG. 4 may also be provided with an end flap 65 as shown in dotted lines in FIG. 5 which may serve as a trap between the last coil and the tip 15a to collect material which might otherwise flow through the openings 50 and coils 42a. Additionally, other means may be provided to form a closed coiled end from that illustrated and still fall within the purvue of the present invention.

While not shown herein, each of the coils 42 may be provided with little external tabs and the wire member 41 may be threaded through the tabs and connected to the tip. Extension of the tip in the forward longitudinal direction slides the wire through the tabs and pulls the coils into a flat narrow diameter insertion position. Rearward movement of the wire through the tabs allows the coils to form and to expand. Other means of connection of the coils to a wire may be provided and still fall within the present invention.

In use, the needle end 13a of the catheter 10 is used to penetrate the vessel 17 and the wire member 20 will be extended as shown in FIG. 1 to uncoil the coils 42 or 42a leaving a straight end portion for threading through the vessel. The tip 15 will be pushed through the embolism 34 or positioned at the location of the plaque and then the wire member 20 will be pulled from the socket 26 in the tip 15 and pulled back through the needle 13 to leave a hollow passageway 21 from the tubular body 25 from the tip 15 to the syringe receptor 27. Removal of the tensioning force from the coil section 30 allows the coils 42 to automatically form and pull the tip rearwardly as the coils form. The operator will then push or pull on the wire member 41 to change the diameters of the coil to suit the diameter of the vessel. To assist in the collection the embolism material or the dilatation of the plaque, the operator will force liquid through the now hollow passageway in the coils 42 and exert hydraulic pressure from the syringe to stiffen and harden the coils. Because of the cone shape defined by the coils 42b–42i and the central wire 41 extending through the embolism material within the coiled section 30, a pulling on the wire 41 will slide the coil section 30 toward the catheter body 13 at the incision area. When the embolism material is adjacent the catheter body end 13a, the wire member 41 may be pushed forwardly causing the coil section to lenthen and contract in diameter. The clot material may now be removed manually through the needle or be sucked through the needle by suction forces.

From the foregoing it will be seen that the present invention provides a new and improved catheter which may be formed inexpensively and which provides an improved means for the collection of material within the living vessel. Additionally, the present invention provides for a coiled expandable and contractable catheter end which may be used for dilatation as well as for removal of material. The particular stiffness of the coils may be readily controlled by control means therefore and the diameter of the coils may be changed.

Although the invention has been described in the terms of these preferred embodiments, it is not intended to limit the invention to these preferred embodiments. On the contrary, it is intended to cover all aspects of the invention covered by the appended claims.

I claim:

1. A catheter for insertion into a living vessel comprising:
    an elongated tube formed of a flexible elastomeric material and having a proximal end and a distal end, an elongated wire member extending longitudinally within the tube from the proximal end of the tube to the distal end and providing rigidity to the catheter to aid in guiding insertion of the catheter into and through the living vessel,
    a coil section on said catheter movable between a first insertion position and a second operative position, said coil section being extended to the insertion position by extension of the wire member to decrease the diameter of the coil portion for insertion into and through the living vessel;
    said coil section being expanded in diameter and into the coiled operative position upon relaxation of the straightening force applied to the coil section by the wire member, and
    an elongated hollow passage way in said tube to receive fluid pressure to stiffen the coil section.

2. A catheter in accordance with claim 1 in which the coil section is preformed with a memory to assume a coiled condition and in which said wire member stretches the coils out longitudinally into a substantially straight uncoiled condition.

3. A catheter in accordance with claim 1 in which said coil section is formed with a conical shape with the smallest coils adjacent the distal end of the catheter to form a hollow scoop to collect and hold blood clot material for removal.

4. A catheter in accordance with claim 1 in which the coil section has a substantially constant diameter for each of its coils.

5. A catheter in accordance with claim 1 including an operating means to expand or contract the diameter of the coils of the coiled section.

6. A catheter in accordance with claim 5 in which the operating means includes a wire member extending to a distal end of the coil section and being pushed or pulled to shift the distal ends of the coil section to cause the coils to expand or to contract in diameter.

7. A catheter in accordance with claim 1 in which a syringe receptor is connected to the catheter body and to a passageway formed in the coils upon removal of the wire member from the coils.

8. A catheter for insertion into a living vessel comprising an elongated tube formed of a flexible elastomeric material and having a proximal end and a distal end, an elongated wire member extending longitudinally within the tube from the proximal end of the tube to the distal end and providing rigidity to the catheter to aid in guiding insertion of the catheter into and through the living vessel, a coiled distal end section on said catheter movable between a first insertion position and a second operative position, said coiled section being extended to the insertion position by extension of the wire member to decrease the diameter of the coiled section for insertion into and through the living vessel, the coil expanding in diameter and into the coiled operative position and a second wire member connected to the distal end of the elongated tube to be pushed or pulled to change the diameter of the coils in the coiled section.

9. A catheter in accordance with claim 8 in which said coiled section is formed with a conical shape with the smallest coils adjacent the distal end of the catheter.

10. A catheter in accordance with claim 8 in which the coiled section has coils of substantially constant diameter.

11. A catheter for insertion into a living vessel comprising a needle having a sharpened end for incision into the vessel, a catheter body of tubular shape within the needle and having first and second bores therein, an elongated tubular member formed of a flexible elastomeric material and having a proximal end extending through a first bore in the catheter body and having a remote distal end, an elongated wire member extending longitudinally within the tubular body from the proximal end to the distal end and providing rigidity to the tubular member to aid in guiding insertion of the latter into and through the living vessel, a coiled distal end portion on said tubular member movable between a first insertion position and a second operative position, said coiled portion being extended to the insertion position by extension of the wire member to decrease the diameter of the coiled portion for insertion into and through the living vessel, the coiled expanding in diameter and into the coiled operative position upon relaxation of the straightening force applied to the coiled portion by the wire member.

12. A catheter in accordance with claim 11 in which said coiled portion is formed with a conical shape with the smallest coils adjacent the distal end of the catheter.

13. A catheter in accordance with claim 11 in which the coiled section has coils of substantially constant diameter.

14. A catheter in accordance with claim 11 in which a second wire extends parallel to and along side of the tubular member, said second wire member extending the distal end from the tubular body to the catheter body through which the second wire member slides, pushing or pulling on the second wire changing the diameters of the coils in the coiled portion.

15. A catheter for insertion into a living vessel comprising:
an elongated tube formed of a flexible elastomeric material and having a proximal end and a distal end, an elongated wire member extending longitudinally within the tube from the proximal end of the tube to the distal end and providing rigidity to the catheter to aid in guiding insertion of the catheter into and through the living vessel,
a coil section on said catheter movable between a first insertion position and a second operative position, said coil section being extended to the insertion position by extension of the wire member to decrease the diameter of the coil portion for insertion into and through the living vessel;
said coil section being expanded in diameter and into the coiled operative position upon relaxation of the straightening force applied to the coil section by the wire member,
said wire member being pulled from the elongated tube leaving a passageway; and means connected to the passageway to apply fluid pressure to the coils to stiffen the same.

16. A catheter for removal of blood clot material from a blood vessel comprising:
an elongated tube formed of elastomeric material,
said tube being wound at its internal end to define a conical coiled section,
said conical coiled section being hollow to form an internal hollow scoop to collect and carry blood clot material when the conical coiled section is pulled in a removal direction,
coils of said conical coiled section having a memory to open to an expanded position to form the scoop with coils of elastomeric material expanding to engage and slide along the interior wall of the blood vessel during clot removal and,
an elongated wire member extending longitudinally with tube from a proximal to a distal end of the tube, said wire being connected to said coiled section and being movable in a first direction to decrease the diameter of the coiled section for insertion into the blood vessel and to provide rigidity to the catheter for facilitating insertion,
said elongated wire member being movable to a second position to allow the coiled section to expand to define the hollow scoop at a location to be cleared of blood clot material.

* * * * *